US005127898A

United States Patent [19]

McConnelll

[11] Patent Number: 5,127,898

[45] Date of Patent: * Jul. 7, 1992

[54] WRAP AND METHOD FOR APPLYING TRACTION

[76] Inventor: Bernard E. McConnelll, P.O. Box 8306, Greenville, Tex. 75401

[*] Notice: The portion of the term of this patent subsequent to Apr. 2, 2008 has been disclaimed.

[21] Appl. No.: 678,809

[22] Filed: Apr. 1, 1991

Related U.S. Application Data

[63] Continuation of Ser. No. 173,440, Mar. 25, 1988, Pat. No. 5,003,067.

[51] Int. Cl.[5] .......................... A61F 5/10; A61F 13/00; A41D 19/00

[52] U.S. Cl. .......................................... 602/19; 2/158; 2/161 A; 606/241; 602/62

[58] Field of Search ................. 128/77, 75, 165, 87 A, 128/381; 2/161 A, 158; 602/19, 62; 606/241

[56] References Cited

U.S. PATENT DOCUMENTS

| | | | |
|---|---|---|---|
| 2,658,510 | 11/1953 | Hilton | 128/165 |
| 3,274,616 | 9/1966 | Russo | 128/165 |
| 3,348,238 | 10/1967 | Hydock | 128/165 |
| 3,547,112 | 12/1970 | Courtney | 128/77 |
| 3,774,242 | 11/1973 | Owen | 128/77 |
| 4,125,257 | 11/1978 | Lew | 128/75 |
| 4,281,647 | 8/1981 | Antypas | 128/77 |
| 5,003,967 | 4/1991 | McConnell | 128/77 |

FOREIGN PATENT DOCUMENTS

| | | | |
|---|---|---|---|
| 104809 | 1/1917 | United Kingdom | 128/77 |

*Primary Examiner*—Edgar S. Burr
*Assistant Examiner*—Kimberly L. Asher
*Attorney, Agent, or Firm*—Dennis T. Griggs

[57] ABSTRACT

A traction wrap for suspending a patient's hand and arm in a substantially elevated position during a surgical procedure includes a hand wrap for maintaining the patient's hand in a closed fist condition. A flexible panel is draped over a bar and is secured to the hand wrap along substantially the entire length of the patient's fist on both the palm and back sides. When the patient's hand is in closed, the fist defines a substantially conical shape. The lifting force exerted by a traction device is applied to the elongated bar and flexible panel member, which in turn applies the lifting force through the wrap substantially uniformly across the conical surface of the patient's closed fist. In this configuration, the lifting force does not exert excess pressure at a particular position, such as on the patient's wrist as in prior art devices, so that the flow of blood to and from the patient's hand and fingers is not constricted. The wrap is applied relatively loosely around the patient's wrist to allow ready access to the wrist bones during a surgical procedure and without restricting blood circulation.

1 Claim, 5 Drawing Sheets

WRAP AND METHOD FOR APPLYING TRACTION

CROSS REFERENCE TO RELATED APPLICATION

This is a continuation of application Ser. No. 07/173,440, filed Mar. 25, 1988, now U.S. pat. No. 5,003,067.

FIELD OF THE INVENTION

The present invention relates generally to traction devices for maintaining a patient's arm and hand in an elevated position and in particular to a traction device which includes a hand wrap to hold the hand and arm in an elevated position without constricting blood circulation.

BACKGROUND OF THE INVENTION

Traction devices are commonly used by surgeons to maintain a limb or extremity in an elevated position during a surgical procedure or during recovery after an operation. For example, if a person has a broken arm, the arm may be elevated by a traction device while the person is reclining on an operating table, in order to immobilize and align the arm so that the fracture can be repaired properly.

DESCRIPTION OF THE PRIOR ART

According to prior practice, traction devices used for retaining the arm in an elevated position typically include a sling which is secured about the wrist for exerting a lifting force on the arm. The pressure caused by this lifting force is directed inwardly around the patient's wrist, thereby tending to cut off the blood circulation to and from the hand and fingers. The blood circulation problem is aggravated by the fact that the arm is held upright, which makes it necessary for the blood to flow through the arteries of the arm against the force of gravity. Another limitation of the prior art traction devices is that distal portions of the radius and ulna bones (i.e., the two bones of the forearm) in the wrist area are enclosed by the traction device, which makes it difficult to gain access to these distal portions if required during a surgical procedure.

There are some traction devices that have localized constriction around the fingers such as the so-called "Chinese Finger Trap" devices that cut off blood circulation, and also there are wrist sling devices which apply localized constricting forces about the wrist and cut off circulation through the wrist.

OBJECTS OF THE INVENTION

It is, therefore, the principal object of the present invention to provide an improved traction device for retaining the arm and hand of a patient in a substantially immobile, elevated position.

Another object of the invention is to provide a hand 1 traction device whereby the hand and fingers are maintained in a closed fist position so that the lifting force of the traction device is applied substantially uniformly across the inverted conical surface defined by the closed fist.

Another object of the invention is to provide a hand wrap which permits traction to be applied as the wrist is manipulated in extension, flexion, ulnar deviation, radial deviation and any combination of those movements.

Another object is to control the various deviations of the wrist while applying traction, and at the same time, permit rotation of the forearm while effecting the foregoing various deviations of the wrist.

Still another object of the invention is to provide a hand traction device which does not constrict to and from the hand and fingers.

A further object of the invention is to provide a hand traction device which provides sufficient radial clearance around the patient's wrist to allow ready access to distal portions of the forearm bones during a surgical procedure.

SUMMARY OF THE INVENTION

The fist may be considered to represent an inverted cone or else an inverted pyramid, which is truncated at the top. Because the traction forces are applied about the inverted conical surface, the radial component of that force is minimized so that the principal force that is directed onto the hand is along the axis of the arm and is not directed radially inwardly. Because the constricting forces are reduced, the wrap of the present invention can support the hand and arm without cutting off blood circulation. That is, the traction force is uniformly spread over the external surface area of the fist rather than being concentrated on one area around the wrist or around the fingers as used in prior art devices.

According to the preferred embodiment of the present invention a hand wrap is provided which includes a relatively flat central member which is applied to the back of a patient's hand so that the major axis of the central member is substantially aligned with the patient's arm and fingers; first and second relatively flat panels depending from opposite sides of a first portion of the central member, third and fourth relatively flat panels depending from opposite sides of a second portion of the central member and fifth and sixth relatively flat panels depending from opposite sides of a third portion of the central member; and means for securing the respective panels in respective predetermined positions when the hand wrap device is wrapped around the patient's hand and wrist to maintain the patient's fingers in a closed fist position with the thumb exposed.

The first and second panels are wrapped around the patient's wrist and a portion of the patient's hand below the proximate end of the thumb so that the distal end of the second panel overlaps the distal end of the first panel. The third and fourth panels are wrapped diagonally across the patient's palm so that the distal ends of the third and fourth panels criss-cross one another and overlap respective portions of the second panel The central member is folded transversely across the patient's wrist to enclose the patient's fingers in the closed fist position with the thumb exposed. The fifth and sixth panels are then wrapped around the central member after the patient's hand is retained in the closed fist position. The hand wrap device is adapted for attachment to a traction device whereby the patient's arm can be elevated by exerting a lifting force which is directed substantially uniformly across the patient's closed fist.

In one embodiment the means for securing the respective panels in respective predetermined fixed positions is comprised of a plurality of first attachment members disposed on respective first major surfaces of said second, third, fourth, fifth and sixth panels and a plurality of second attachment members disposed on respective second major surfaces of the central member and the first, second and sixth panels, the second attachment members being complementary with the first attachment members for engaging respective ones of the first attachment members to provide a relatively secure attachment therebetween. The distal end of the fifth panel overlaps the distal end of the sixth panel and is secured thereto by means of the complementary attachment members.

In another embodiment, means is provided for attaching the hand wrap to a traction support member. The attaching means includes a relatively rigid bar, coupled to the traction support member for being positioned in contact with the second major surface of the central member on the patient's fist and a flexible panel for being draped over the bar so that the panel envelopes the patient's hand in the closed fist position along the major axis of the central member. The bar has a first attachment member on a first surface thereof which is in contact with the central member for engaging the complementary second attachment member on a second surface thereof opposite from the first surface. The flexible panel has a first attachment member on a major surface thereof which is in facing relationship with the second surface of the bar and the central member for engaging the complementary second attachment members on the second surface of the bar and on the central member to secure the hand wrap device to the traction support member.

In the preferred embodiment, a predetermined clearance is maintained between the patient's wrist and the hand wrap when the first and second panels are wrapped around the wrist so as not to constrict the flow of blood to and from the patient's hand and fingers. The panels are substantially co-planar with the central member when the hand wrap device is positioned on a relatively flat support surface. The first, second, fifth and sixth panels are tapered so that portions thereof adjacent to the respective distal ends of said first, second, fifth and sixth panels are narrower than the portions thereof adjacent to the respective proximate ends thereof, as measured along respective axes parallel to the major axis of the central member Each of the first attachment members preferably has a plurality of hooks projecting therefrom and each of the second attachment members preferably has a plurality of loops projecting therefrom for engaging the hooks of the corresponding first attachment member to form a secure bond when the corresponding hooks and loops are pressed into contact.

BRIEF DESCRIPTION OF THE DRAWINGS

Other objects and advantages of the invention will be apparent from the detailed description and claims when read in conjunction with the accompanying drawings wherein:

DETAILED DESCRIPTION OF THE PREFERRED EMBODIMENT

In the description which follows like parts are marked throughout the specification and drawings, respectively. The drawings are not necessarily to scale and in some instances proportions have been exaggerated in order to more clearly depict certain features of the invention.

Figure 1:
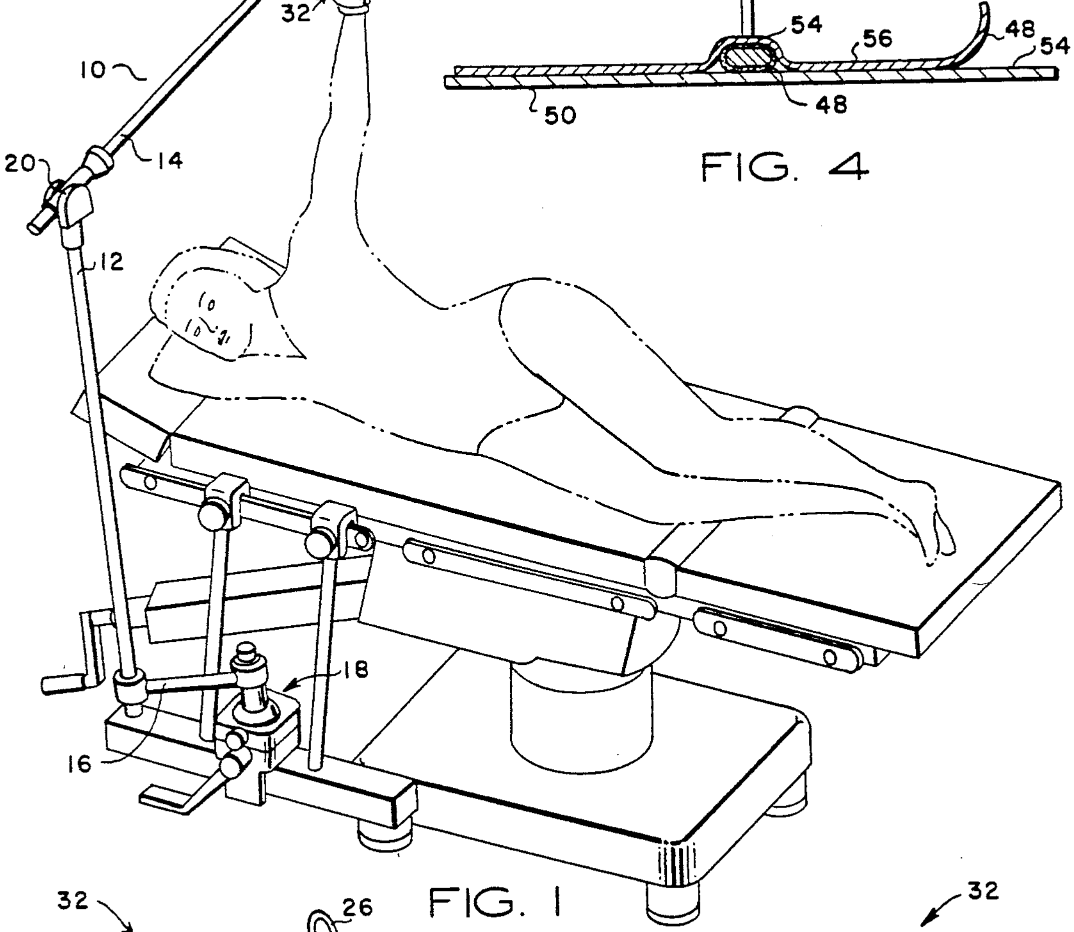
FIG. 1 is a perspective view showing a patient's arm being maintained in an elevated position by means of a traction support member according to the present invention.

Referring to FIG. 1, a traction support member 10 for holding an individual's arm and hand in an elevated position is depicted. Traction support member 10 includes an upright member 12, which is disposed between first and second transverse members 14 and 16. Traction support member 10 is movable about a vertical axis universal positioner 18 and first transverse member 14 is movable about a horizontal axis through attachment coupling 20 at which first transverse member 14 is attached to upright member 12.

The end of first transverse member 14 opposite from attachment point 20 has a curved portion 22 on which a pair of rings 24 and 26 are disposed. Rings 24 and 26 are in engagement so that ring 26 hangs from ring 24. A cord member 28 is provided for suspending an elongated bar 30 from ring 26. The central portion of cord member 38 passes through ring 26 and the respective opposite ends of cord member 28 are affixed to respective opposite ends of bar 30 to define a trapeze-like configuration. A hand wrap 32 is used to retain the patient's hand in a closed fist position and to attach the patient's hand to bar 30 so that traction support member 10 maintains the patient's arm and hand in an elevated position at a desired orientation.

Most of the hand positioning is provided by the hand wrap assembly not the lower attachment structure. The pivoting and swiveling occurs at the attachment point off of the U-hook 22 and not down on the universal positioner 18. The pivot coupling is made by the snap ring 26 that has a swivel feature and the swivel hangs from the support hook 22.

Figure 4:
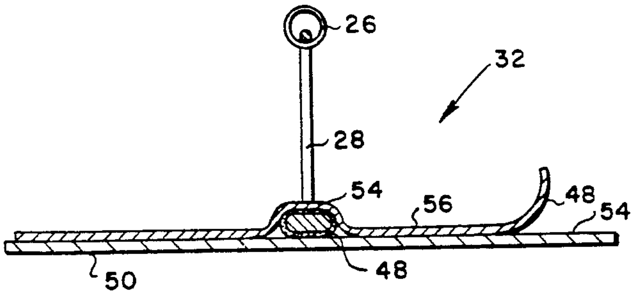
FIG. 4 is a sectional view of the hand wrap device, taken along the line 4—4 in FIG. 2.
Figure 2:
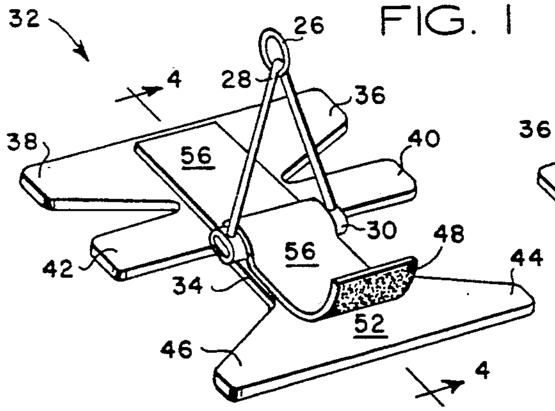
FIGS. 2 and 3 are perspective views from opposite sides of a hand wrap according to the present invention showing the device when it is not in use.
Figure 3:
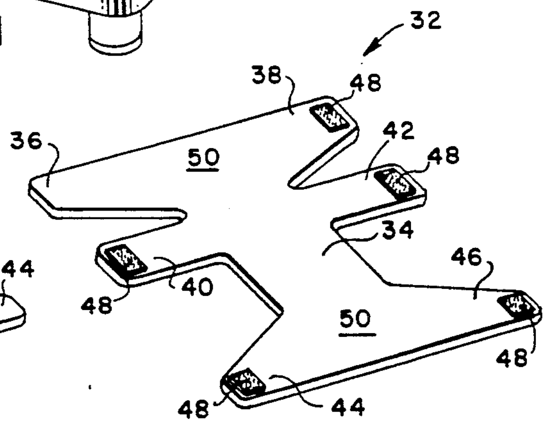

Referring to FIGS. 2-4, the hand wrap 32 is comprised of a relatively flat elongated central hose member 34 and fir second, third, fourth, fifth and sixth relatively flat panel flaps 36, 38, 40, 42, 44 and 46, respectively, which depend outwardly from central member 34. The central member 34 is preferably constructed of closed cell polymer foam material. First and second panels 36 and 38 extend outwardly from central member 34 on respective opposite sides thereof to form a first cooperating pair of panels; third and fourth panels 40 and 42 extend outwardly from central member 34 on respective opposite sides thereof to form a second pair of cooperating panels; and fifth and sixth panels 44 and 46 extend outwardly from central member 34 on opposite sides thereof to define a third pair of cooperating panels.

The panel flaps are co-planar with central member 34 when hand wrap 32 is disposed on a relatively flat support surface, as in FIGS. 2–4, and the panels are oriented so that an axis connecting the respective distal ends of the individual panels in each cooperating pair is substantially orthogonal with respect to the major axis of central member 34. First, second, fifth and sixth panels 36, 38, 44 and 46, respectively, are tapered so that the respective distal ends thereof are substantially narrower than the respective proximate ends thereof, as measured along respective axes which are parallel to the major axis of central member 34.

Referring to FIG. 3, a plurality of attachment members having a first attachment material 48 are disposed on a first major surface 50 of hand wrap 32, adjacent to respective distal ends of second, third, fourth, fifth and sixth panels 36, 40, 42, 44 and 46, respectively. Referring to FIG. 2, a second major surface 52, opposite from first major surface 50, includes a second attachment material 54, which is complementary with first attachment material 48 for engaging first attachment material 48 when the individual panels are wrapped around the patient's hand and wrist, as will be described in greater detail hereinafter. First attachment material 48 is comprised of a plurality of hook-like elements of resilient material, as best seen in FIG. 3, and second attachment material 54 has a pile fabric face with a plurality of loop elements.

Pressing first and second attachment materials 48 and 54 together produces an intermeshing or locking of the hooks and loops to provide a bond of significant strength and shear. Material which is suitable for the first and second attachment materials 48 and 54 is sold by Velcro Corporation under the trademark "VELCRO". One skilled in the art will appreciate that the materials comprising first and second attachment materials 48 and 54 can be switched (i.e., loops can be substituted for the hooks in first attachment material 38 and hooks can be substituted for the loops in second attachment material 54).

After the patient's hand and wrist are enclosed by hand wrap 32 in a closed fist position, hand wrap 32 is secured to a lower surface (as viewed in FIG. 1) of bar 30 by positioning second major surface 52 in contact with the lower surface of bar 30, as best seen in FIG. 4. The lower surface of bar 30 is substantially comprised of first attachment material 48 for engaging second attachment material 54 on second major surface 52 to maintain hand wrap 32 in a fixed position relative to bar 30 An elongated flexible panel 56 is draped over an upper surface of bar 30 so that substantially equal portions of flexible panel 56 overlap bar 30 on either side. The major surface of flexible panel 56 which is in facing relationship with second major surface 52 is substantially comprised of first attachment material 48 for engaging the complementary second attachment material 54 on second major surface 52 and on the upper surface of bar 30 when flexible panel 56 contacts second major surface 52 after being draped over bar 30. In this manner, hand wrap 32 is held in a predetermined fixed position relative to bar 30.

Figure 5:
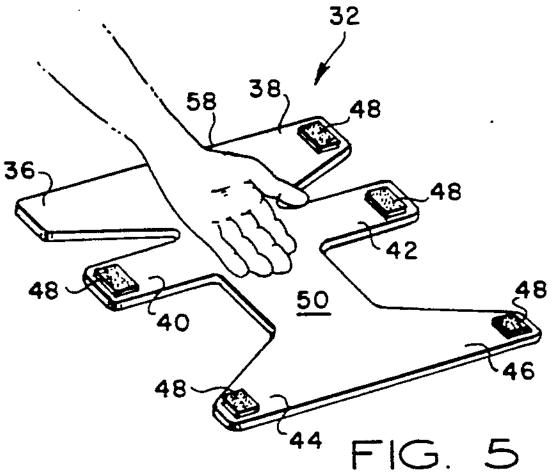
FIGS. 5-10 are perspective views illustrating the procedure by which the hand device according to the present invention is wrapped around a patient's hand to maintain the patient's hand in a closed fist position with the thumb exposed.

Referring to FIGS. 5–13, the procedure by which the patient's hand is wrapped and attached to bar 30 of traction device 10 is depicted in detail. Hand wrap 32 is preferably placed on a relatively flat support surface with all of its panels fully extended, as shown in FIG. 5. The patient's hand and wrist are placed on top of hand wrap 32 so that the back of the patient's hand is in contact with first major surface 50. The patient's hand is positioned such that the patient's wrist is substantially coterminous with proximate edge 58 of wrap 32.

Figure 6:
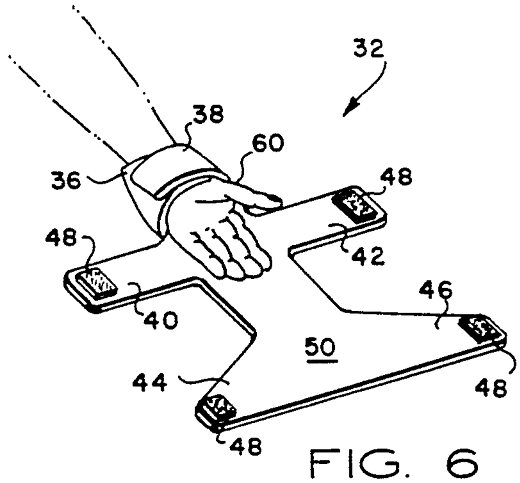
Figure 7:
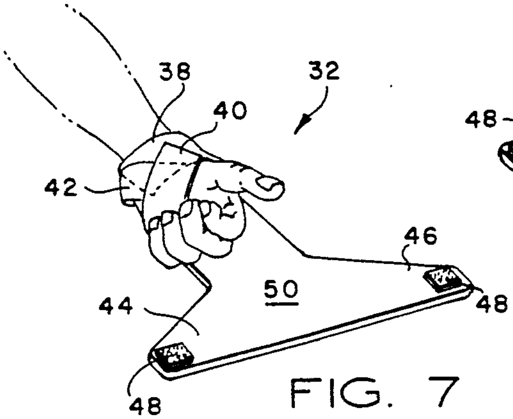

Referring to FIG. 6, first and second panels 36 and 38 are wrapped around the patient's wrist and the portion of the patient's hand just below proximate end 60 of the patient's thumb so that the distal end of second panel 38 overlaps the distal end of first panel 36. The member comprising first attachment material 48 on second panel 38 engages the complementary second attachment material 54 on first panel 36. Referring to FIG. 7, third and fourth panels 40 and 42 are wrapped diagonally across the patient's palm so that the respective distal ends of third and fourth panels 40 and 42 criss-cross one another with third pane 40 overlapping fourth panel 42. The respective members comprising attachment members 48 on third and fourth panels 40 and 42 engage the complementary second attachment material 54 on second panel 38 to secure third and fourth panels 40 and 42.

Figure 8:
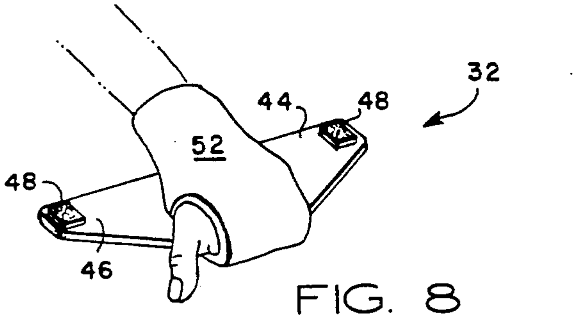
Figure 10:
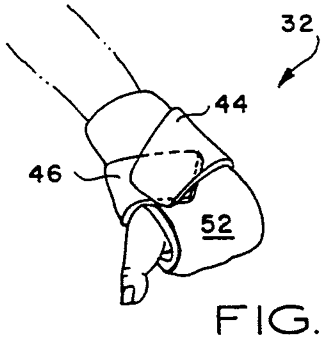
Figure 9:
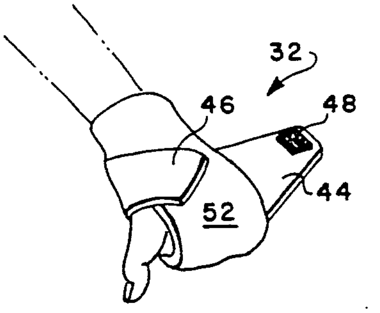
Figure 16:
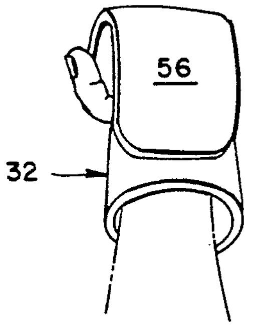
Figure 17:
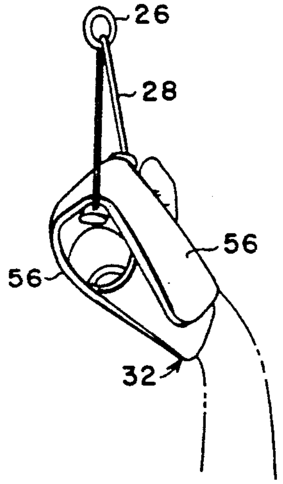

The patient's fingers are then flexed to define a closed fist position with the thumb extending outwardly, as shown in FIG. 7. Referring now to FIGS. 8-10,. the portion of central member 34 which is beyond the patient's fingers and fifth and sixth side strip panels 44 and 46 are folded along the major axis of central member 34 in the direction of the user's wrist to envelope the user's hand in the closed fist position so that first major surface 50 is in contact with the patient's fist and second major surface 52 is exposed. The primary function of the side straps 44, 46 of the wrap is to maintain the fingers in the flexed position and will be fully flexed at the knuckles. Fifth and sixth panels 44 and 46 are then wrapped around the patient's fist so that first attachment material 48 on sixth panel 46 is secured to the complementary second attachment material 54 on second major surface 52 and the distal end of fifth panel 44 overlaps the distal end of sixth panel 46 and first attachment material 48 on fifth panel 44 engages the complementary second attachment material 54 on sixth pane 46 (as shown in FIG. 10). At this juncture, hand wrap 32 is completely secured around the patient's wrist and hand. As best seen in FIG. 16, first and second panels 36 and 38 are wrapped around the patient's wrist and hand wrap 32 to allow access to the patient's wrist during a medical procedure and to allow blood circulation to and from the patient's hand and fingers.

Figure 11:
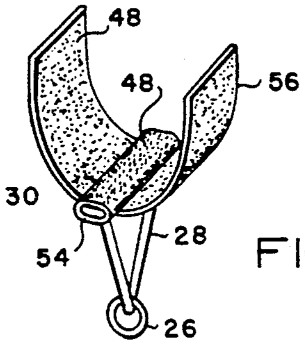
FIGS. 11-13 are perspective views illustrating the procedure by which the hand wrap is attached to a traction support member after the patient's hand is retained in the closed fist position.
Figure 12:
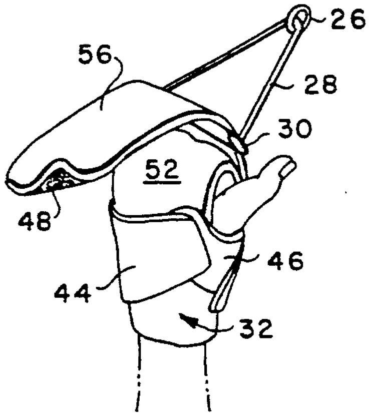
Figure 13:
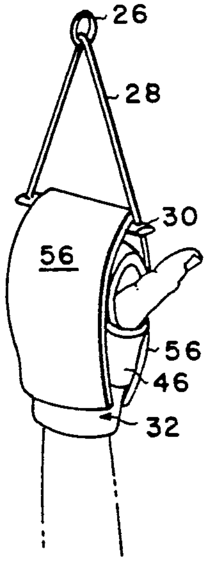

Referring to FIGS. 11–13, the patient's hand, with hand wrap 32 disposed thereon, is attached to traction device 10. The fist portion of the patient's hand is placed in abutting relationship with the lower surface of bar 30 so that first attachment material 48 on the lower surface of bar 30 engages the complementary second attachment material 54 on hand wrap 32, as best seen in FIG. 12. A flexible coupling panel 56 is then draped over bar 30, as described above with reference to FIGS. 2–4, so as to envelope the patient's hand on both the palm and back portions thereof, as best seen in FIG. 13. First attachment material 48 comprising the facing major surface of flexible panel 56 engages the complementary second attachment material 50 on hand wrap 32 along substantially the entire length of the patient's hand on both the palm and back portions thereof to secure the patient's hand in the closed fist position to traction device 10.

The lifting force exerted by traction device 10 is transmitted by bar 30 to flexible panel 56, which in turn exerts a lifting force on the patient's hand and arm by directing the lifting force substantially uniformly around the entire area of the patient's closed fist. When the patient's hand is flexed in the closed fist position as shown, the hand defines a substantially conical shape, which tends to more equally distribute the lifting force across the hand so that excess pressure is not applied at any particular location on the hand or wrist.

Figure 14:
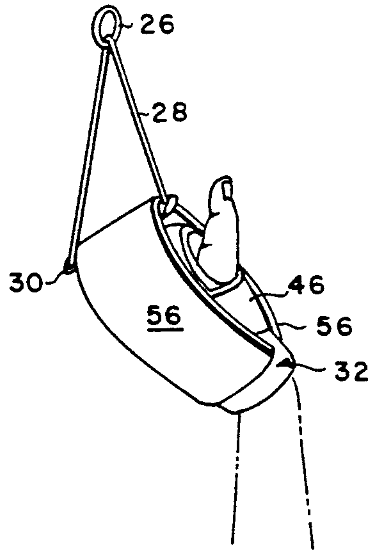
FIGS. 14-22 are perspective views illustrating the various positions in which the patient's hand and arm can be retained.
Figure 15:
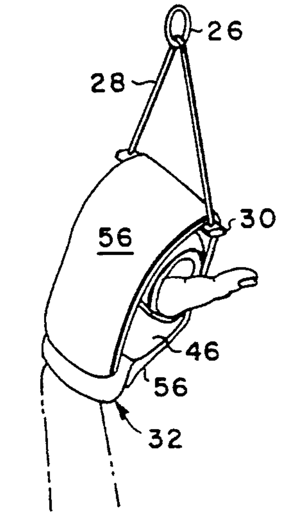

FIGS. 13–21 show various positions in which the patient's hand and arm can be retained by the traction device. In FIG. 13 the patient's hand and arm are held substantially vertically so that straight line traction is applied equally to both the radius and ulna bones of the forearm. In the event of a radius fracture, the wrist will be deviated toward the ulna side in order to align the radius bone, as shown in FIG. 14. Similarly, in the event of a ulna fracture the wrist is deviated toward the radius side in order to align the ulna.

FIGS. 16–22 show other positions in which the patient's hand and arm can be retained by the traction device according to the present invention. One skilled in the art will appreciate that the patient's hand may be maintained in a flexed or aligned position relative to the patient's arm by adjusting the relative position on the patient's fist at which bar 30 is attached and that the orientation of the patient's arm and hand relative to a vertical axis may be adjusted by varying the position at which cord member 28 is attached to ring 26.

Figure 18:
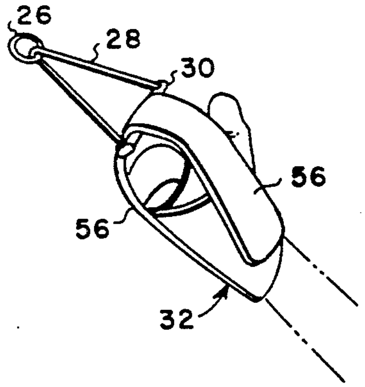
Figure 19:
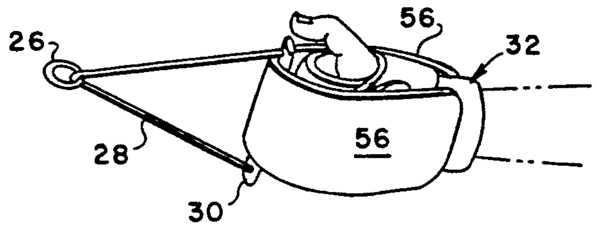
Figure 20:
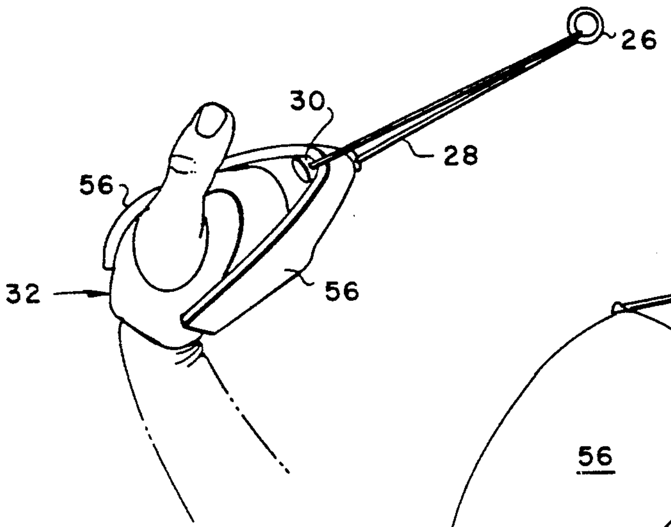
Figure 21:
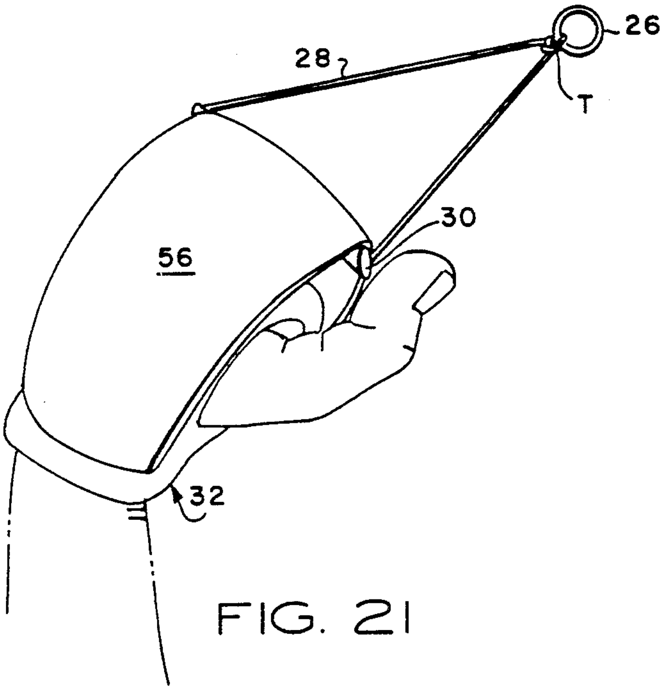
Figure 22:
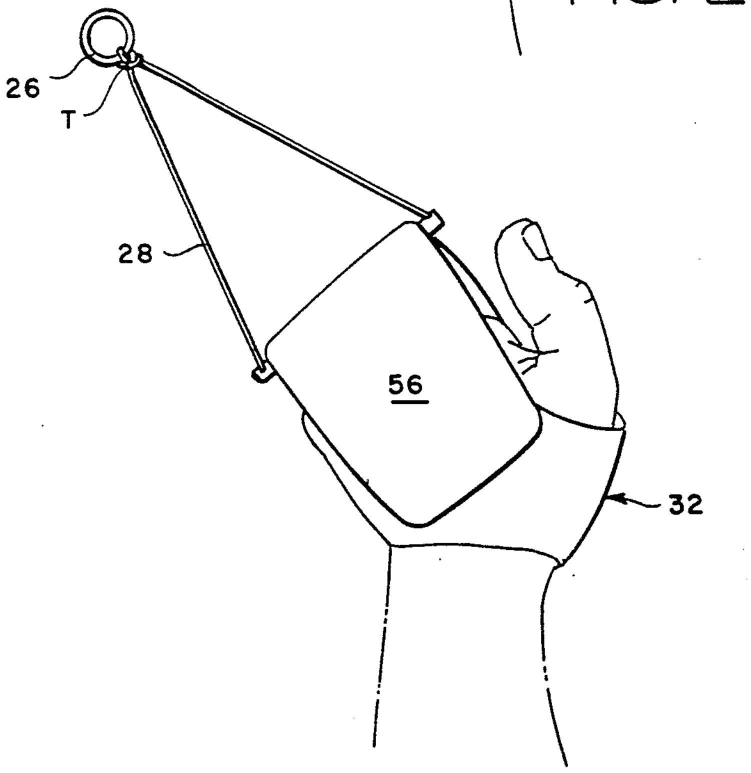
Figure 23:
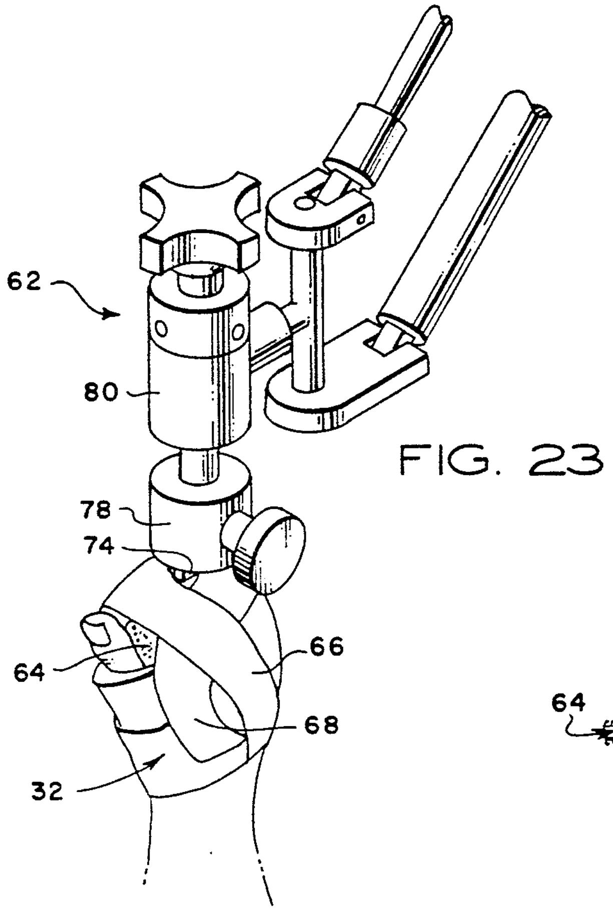
FIG. 23 is a perspective view illustrating an alternative arrangement for attaching the hand wrap of the present invention to a traction support member.
Figure 24:
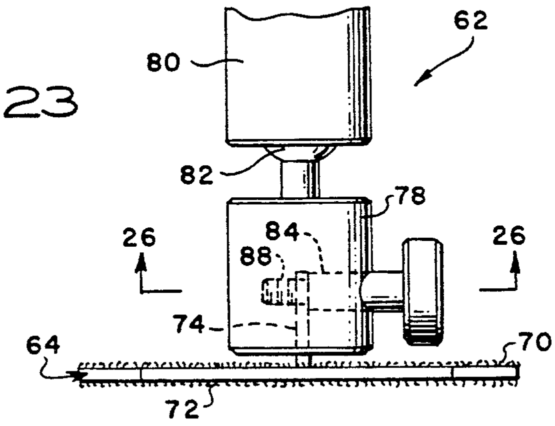
FIG. 24 is an elevation view, partially broken away, of the coupling assembly shown in FIG. 23.
Figure 25:
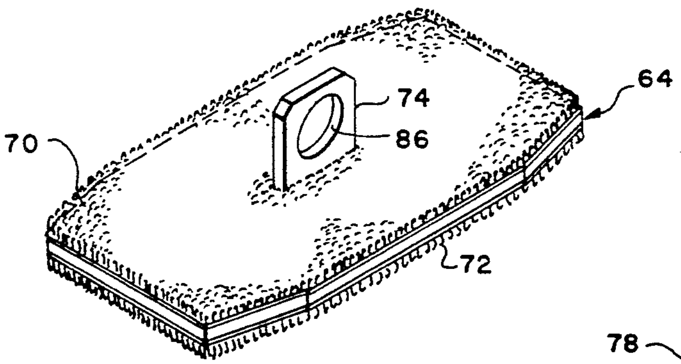
FIG. 25 is a perspective view of a coupling plate which forms a part of the coupling assembly shown in FIG. 24; and, FIG. 26 is a sectional view of the coupling assembly taken along the lines 26—26 as shown in FIG. 24.
Figure 26:
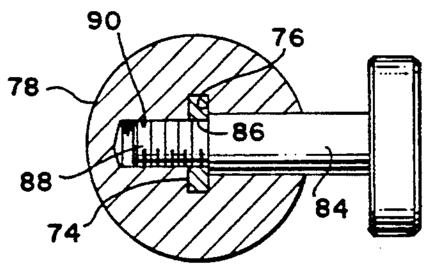

For example, in FIGS. 18, 19 and 20, cord member 28 is coupled to ring 26 so that cord member 28 is disposed at an angle relative to the vertical axis. The traction force is therefore exerted along an axis connecting ring 26 and the approximate geometric center of bar 30 to retain the patient's hand and arm at the same angle relative to the vertical axis. Cord member 28 is preferably secured to ring 26 by a tie knot T at a desired position, for example as shown in FIGS. 21, 22 so that cord member 28 does not slip. One arm of the cord 28 is made longer than the other and affixed to the ring with one section long and the other one short. This will permit a vertical pull or by the moving it to the ulna side to deviate it toward the radius side.

By placing the bar 30 toward the palm side, the vertical traction brings the wrist into extension. When the vertical bar 30 is affixed to the back of the hand, wrist flexion will be produced.

Referring now to FIGS. 23–26, an alternative method for attaching the hand wrap 32 to a traction support member 62 is illustrated. The traction support member includes a coupling plate 64 which is attached onto the hand wrap surface 50 by auxiliary crossover straps 66, 68. The auxiliary crossover straps 66, 68 have a VELCRO pile hook layer for engaging and interlocking with the VELCRO pile loop layer on the external surface of the hand wrap 52.

A VELCRO pile hook layer 70 is attached to the upper planar surface of the coupling plate 64, and a VELCRO pile loop layer 72 is attached to the bottom planar surface of the coupling plate 64. A lug 74 is centrally mounted onto the coupling plate 64 and projects upright through the pile hook layer 70 for insertion into a keyway 76 formed within a coupling collar 78. The 1 coupling collar 78 is attached to a releasable ball clamp assembly 80. The ball clamp assembly 80 is preferably constructed as shown in my U.S. Pat. No. 4,708,510 entitled "BALL JOINT COUPLING", which is hereby incorporated by reference.

The clamp assembly 80 utilizes a ball member 82 which can be released and positioned as desired to manipulate the patient's hand relative to the wrist in extension, flexion, ulnar deviation, radial deviation, or any combination of those movements while applying traction through the hand and wrist.

The coupling plate 64 is pressed onto the top surface 52 of the wrapped fist which causes an intermeshing or locking of the VELCRO loops 72 with the hooks on surface 52 to provide a bond of significant strength and shear. The auxiliary straps 66, 68 are crossed over the upper VELCRO pile loop layer 70 and are wrapped about the conical hand wrap surface 52.

After the patient's hand and the hand wrap have been secured to the coupling plate 64, the coupling assembly is locked onto the coupling collar 78 by inserting the lug 74 into the keyway 76. The lug 74 is locked in place by a pin 84 which is inserted through the collar 78 and through a locking aperture 86 formed in the lug 74. The pin 84 has a threaded end portion 88 received in threaded engagement with a threaded counterbore 90 formed in the coupling collar 78. According to this arrangement, the coupling plate 64 is securely joined to the coupling collar 78 whereby traction forces applied by the traction support member 62 are efficiently transmitted through the clamp assembly, lug and coupling plate to the hand traction wrap 32 and the patient's fist.

According to the foregoing embodiments, traction is applied to an inverted conical surface which the fist presents whenever the fingers are fully flexed at the knuckles. After a fist has been made, an inverted conical surface is produced that transitions gradually from the wrist upwardly to the knuckles. Additionally, after the wrap has been secured in place about the conical surface of the fist, the wrap maintains the fist in the closed position, and prevents the hand from opening up while it is being suspended. The wrap distributes the traction forces across the conical surface of the closed fist with the forces applied onto the wrap being relatively smaller near the junction of the wrist and becoming relatively greater in magnitude toward the top of the fist. The radially inwardly directed forces which prevent the wrap from being pulled off of the wrist are applied through the wrap rather than being focused on the wrist or some other localized point of application. The traction force applied to the wrap through bar 30 produces a shear force along the conical surface of the closed fist.

The wrap produces points of pressure onto the external surface of the fist which can be resolved into a force normal to the traction force and a shear force approximately parallel to the traction force. The resultant vector of forces directs the pressure against the inclined plane of the conical surfaces of the fist so that with the conical fist surface being inverted, the linear traction force on bar 30 is counteracted.

Various embodiments of the invention have now been described in detail. Since changes in and modifications to the above-described preferred embodiment may be made without departing from the nature, spirit and scope of the invention, the invention is not to be limited to said details, except as 1 set forth in the appended claims.

What is claimed is:

1. A method for supporting a patient's hand an arm in a substantially elevated position, said method comprising the steps:

providing a traction wrap for attachment to the patient's hand, said traction wrap including a flexible base panel member having a proximal end portion, a middle portion and a distal end portion;

folding the base panel member about the patient's closed fist with the proximal end portion of the base panel member overlapping the patient's wrist and the back of the patient's hand, the middle of the base panel member overlapping the patient's flexed fingers and knuckles, and the distal end portion of the base panel member overlapping the base of the patient's hand and wrist;

securing the proximal, middle and distal end portions of the base panel member in wrapped engagement about the patient's closed fist, with the proximal end portion of the base panel member and the distal end portion of the base panel member in combination providing an enclosing sidewall which conforms about the external surface of the patient's closed fist, with the enclosing sidewall transitioning gradually from the patient's wrist to the patient's knuckles; and, applying a traction force through the enclosing sidewall.

* * * * *

UNITED STATES PATENT AND TRADEMARK OFFICE
CERTIFICATE OF CORRECTION

PATENT NO. : 5,127,898

DATED : July 7, 1992

INVENTOR(S) : Bernard E. McConnell

It is certified that error appears in the above-identified patent and that said Letters Patent is hereby corrected as shown below:

Column 1, line 60, "1 traction" should be -- traction --.

Column 2, line 51, "second panel The" should be -- second panel. The --.

Column 3, line 41, "central member Each" should be -- central member. Each --.

Column 4, line 60, "and fir second" should be -- and first, second --.

Column 5, line 54, "30 An" should be -- 30. An --.

Column 6, line 43, "sixth pane" should be -- sixth panel --.

Column 7, line 66, "The 1 coupling" should be -- The coupling --.

Column 8, line 66, "except as 1 set" should be -- except as set --.

UNITED STATES PATENT AND TRADEMARK OFFICE

CERTIFICATE OF CORRECTION

PATENT NO. : 5,127,898 Page 2 of 2

DATED : July 7, 1992

INVENTOR(S) : Bernard E. McConnell

It is certified that error appears in the above-indentified patent and that said Letters Patent is hereby corrected as shown below:

Column 9, line 1, "hand an arm" should be -- hand and arm --.

Signed and Sealed this

Fifth Day of October, 1993

Attest:

BRUCE LEHMAN

Attesting Officer

*Commissioner of Patents and Trademarks*